United States Patent
Wang et al.

(10) Patent No.: US 10,070,813 B2
(45) Date of Patent: Sep. 11, 2018

(54) PHOTOACOUSTIC AND THERMOACOUSTIC TOMOGRAPHY FOR BREAST IMAGING

(71) Applicant: Washington University, St. Louis, MO (US)

(72) Inventors: Lihong Wang, St. Louis, MO (US); Geng Ku, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 0 days.

(21) Appl. No.: 15/235,849

(22) Filed: Aug. 12, 2016

(65) Prior Publication Data

US 2016/0345886 A1 Dec. 1, 2016

Related U.S. Application Data

(63) Continuation of application No. 11/625,099, filed on Jan. 19, 2007, now Pat. No. 9,439,571.

(60) Provisional application No. 60/760,612, filed on Jan. 20, 2006.

(51) Int. Cl.
*A61B 5/00* (2006.01)
*A61B 8/08* (2006.01)

(52) U.S. Cl.
CPC .......... *A61B 5/4312* (2013.01); *A61B 5/0091* (2013.01); *A61B 5/0093* (2013.01); *A61B 5/0095* (2013.01); *A61B 8/08* (2013.01)

(58) Field of Classification Search
CPC ................................................. A61B 5/4312
See application file for complete search history.

(56) References Cited

U.S. PATENT DOCUMENTS

| | | | |
|---|---|---|---|
| 3,963,933 A | | 6/1976 | Henkes |
| 4,130,112 A | * | 12/1978 | Frazer .................. A61B 8/0825 |
| | | | 128/915 |
| 4,546,771 A | | 10/1985 | Eggleton et al. |
| 5,242,438 A | * | 9/1993 | Saadatmanesh ....... A61B 18/24 |
| | | | 606/15 |
| 5,713,356 A | | 2/1998 | Kruger |
| 5,860,934 A | | 1/1999 | Sarvazyan |
| 5,971,998 A | | 10/1999 | Russell et al. |
| 6,102,857 A | | 8/2000 | Kruger |

(Continued)

FOREIGN PATENT DOCUMENTS

WO    2008062354 A1    5/2008

OTHER PUBLICATIONS

Kruger et al., "Breast cancer in vivo: contrast enhancement with thermoacoustic CT at 434 MHz-feasibility study," Radiology, 216(1): 279-283 (2000).

(Continued)

*Primary Examiner* — Rochelle Turchen
(74) *Attorney, Agent, or Firm* — Armstrong Teasdale LLP

(57) ABSTRACT

A system for imaging a biological sample including a tubular body having a side wall defining an interior shaped and sized for receiving the biological sample, an electromagnetic source positioned at one end of the tubular body interior for directing electromagnetic energy into the biological sample in the body interior, and an ultrasonic transducer positioned along said side wall of the body for receiving ultrasonic energy induced by the electromagnetic energy and transmitted through the biological sample.

15 Claims, 14 Drawing Sheets

(56) References Cited

U.S. PATENT DOCUMENTS

| | | | |
|---|---|---|---|
| 6,104,942 | A | 8/2000 | Kruger |
| 6,216,025 | B1 | 4/2001 | Kruger |
| 6,292,682 | B1 | 9/2001 | Kruger |
| 6,409,668 | B1 | 6/2002 | Wollschlaeger |
| 6,490,470 | B1 | 12/2002 | Kruger |
| 7,841,982 | B2 | 11/2010 | Johnson et al. |
| 2003/0097066 | A1 | 5/2003 | Shelby et al. |
| 2003/0128626 | A1* | 7/2003 | Verkerk .............. B01F 13/0818 366/140 |
| 2004/0064046 | A1 | 4/2004 | Shehada |
| 2006/0184042 | A1 | 8/2006 | Wang et al. |
| 2006/0235299 | A1 | 10/2006 | Martinelli |
| 2007/0213590 | A1 | 9/2007 | Squicciarini |
| 2007/0250047 | A1 | 10/2007 | Harter |
| 2007/0282200 | A1 | 12/2007 | Johnson et al. |
| 2009/0116518 | A1 | 5/2009 | Patel et al. |

OTHER PUBLICATIONS

Kruger et al., "Thermoacoustic computed tomography using a conventional linear transducer array," Medical Physics, 30(5): 856-860 (2003).

Kruger et al., "Thermoacoustic computed tomography-technical considerations," Medical Physics, 26(9): 1832-1837 (1999).

Kruger et al., "Thermoacoustic Molecular Imaging of Small Animals," Molecular Imaging, 2(2): 113-123 (2003).

Ku et al., "Deeply penetrating photoacoustic tomography in biological tissues enhanced with an optical contrast agent," Optics Letters, 30(5): 507-509 (2005).

Ku et al., "Scanning microwave-induced thermoacoustic tomography: Signal, resolution, and contrast," Medical Physics, 28(1): 4-10 (2001).

Ku et al., "Scanning thermoacoustic tomography in biological tissue," Medical Physics, 27(5): 1195-1202 (2000).

Ku et al., "Imaging of tumor angiogenesis in rat brains in vivo by photoacoustic tomography," Applied Optics, 44(5): 770-775 (2005).

Ku et al., "Multiple-bandwidth photoacoustic tomography," Physics in Medicine and Biology, 49(7): 1329-1338 (2004).

Ku et al., "Thermoacoustic and photoacoustic tomography of thick biological tissues toward breast imaging," Technology in Cancer Research and Treatment, 4(5): 559-566 (2005).

Wang et al., "Noninvasive photoacoustic angiography of animal brains in vivo with near-infrared light and an optical contrast agent," Optics Letters, 29(7): 730-732 (2004).

Wang et al., "Three-dimensional laser-induced photoacoustic tomography of mouse brain with the skin and skull Intact," Optics Letters, 28(19): 1739-1741 (2003).

Office Action issued in related U.S. Appl. No. 13/143,832, dated Apr. 18, 2014 (14 pages).

Office Action issued in related U.S. Appl. No. 13/450,793, dated Nov. 22, 2013 (22 pages).

Office Action issued in related U.S. Appl. No. 13/450,793, dated Mar. 24, 2014 (22 pages).

* cited by examiner

PHOTOACOUSTIC AND THERMOACOUSTIC TOMOGRAPHY FOR BREAST IMAGING

CROSS-REFERENCE TO RELATED APPLICATIONS

This application is a continuation of U.S. application Ser. No. 11/625,099, filed Jan. 19, 2007, which claims the benefit of U.S. Provisional Application No. 60/760,612, filed Jan. 20, 2006, both of which are hereby incorporated by reference herein in their entirety.

STATEMENT REGARDING FEDERALLY SPONSORED RESEARCH OR DEVELOPMENT

This invention was made with government support under a grant from National Institutes of Health (Contract Nos. R01 EB000712 and R01 NS046214). The U.S. government has certain rights in this invention.

BACKGROUND

This invention generally relates to imaging technologies and, more particularly, to apparatus for imaging biological tissue samples such as a breast of a living human using techniques such as photoacoustic or thermoacoustic tomography.

A variety of different devices have been developed for imaging biological samples such as breast tissue. One example of such imaging technology is X-ray mammography. This technology has been used for some time to detect soft tissue anomalies that may indicate breast cancer. Early detection and treatment significantly improves prognoses. As a result of this technology, countless deaths due to breast cancer have been avoided.

One drawback of conventional mammography techniques is that the tissue must be relatively thin to obtain meaningful results, requiring tightly squeezing the breast between a pair of plates. A radiographic source is positioned on one side of the plates and a radiographic detector is positioned on the other side of the plates so an image radiographic image can be obtained. Squeezing the breast can be painful for the person being screened. As a result, some women do not receive mammography screening as frequently as recommended and other women avoid screenings all together. Thus, mammography is less successful than it might be if the procedure was less painful. In addition, mammography involves the use of ionizing radiation, which carries a risk of causing cancer. Accordingly, there is a need for a imaging technique that offers high resolution detection but avoids causing the patient pain.

Thermoacoustic tomography and photoacoustic tomography are techniques in which electromagnetic impulses are directed toward soft tissue to induce ultrasonic waves in the tissue. The ultrasonic waves are measured to determine dielectric and/or optical properties of the tissue. These properties are related to the physiological and pathological health of the tissue. Thermoacoustic tomography uses electromagnetic radiation in the radiofrequency and/or microwave bands, and photoacoustic tomography uses electromagnetic radiation in the visible light and/or near infrared light bands to induce the ultrasonic waves in the tissue. These non-invasive and non-ionizing imaging techniques have a potential to provide high imaging contrast and improved and more accurate cancer diagnoses.

BRIEF SUMMARY

The present invention relates to a system for imaging a biological sample comprising a tubular body having a side wall defining an interior shaped and sized for receiving the biological sample, an electromagnetic source positioned at one end of the tubular body interior for directing electromagnetic energy into the biological sample in the body interior, and an ultrasonic transducer positioned along said side wall of the body for receiving ultrasonic energy induced by the electromagnetic energy and transmitted through the biological sample.

In another aspect, the present invention relates to a system for imaging a breast of a patient comprising a support sized and shaped for contacting the patient around the breast, and a cylindrical body mounted on the support having a side wall. The side wall includes an ultrasonically transparent upper portion defining an interior sized and shaped for receiving the breast of the patient when the support contacts the patient around the breast and a lower portion adjacent the upper portion. The system also includes a plurality of ultrasonic transducers positioned radially outward from the ultrasonically transparent upper portion of the cylindrical body side wall, and a piston slideably mounted in the lower portion of the cylindrical body side wall for movement toward and away from the upper portion of the cylindrical body to position the breast in the interior of the upper portion of the cylindrical body side wall. Further, the system includes equipment positioned axially downward from the piston for directing radiation through the piston and into the breast to excite an ultrasonic response in the breast.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
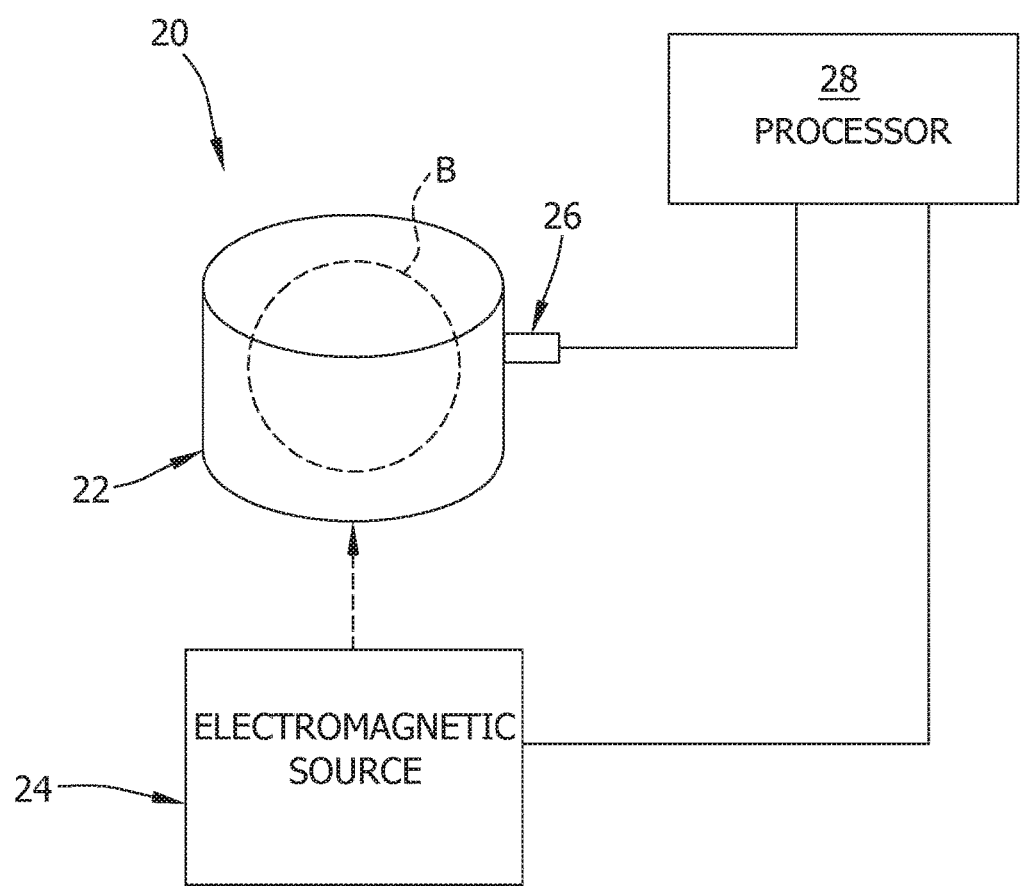
FIG. 1 is a schematic representation of a system for imaging a biological sample according to the present invention.

Referring to the figures, and more particularly to FIG. 1, a system for imaging a biological sample according to a first embodiment of the present invention is designated in its entirety by reference number 20. The system 20 generally comprises apparatus (generally designated by 22) for constraining a biological sample (designated B), an electromagnetic source (generally designated by 24) for emitting electromagnetic energy into the biological sample, and a plurality of ultrasonic transducers (generally designated by 26) for receiving ultrasonic energy induced by the electromagnetic energy and transmitted through the biological sample. A processor 28, such as a conventional personal computer, may be used to control the electromagnetic source 24 and process signals from the ultrasonic transducer 26.

Figure 2:
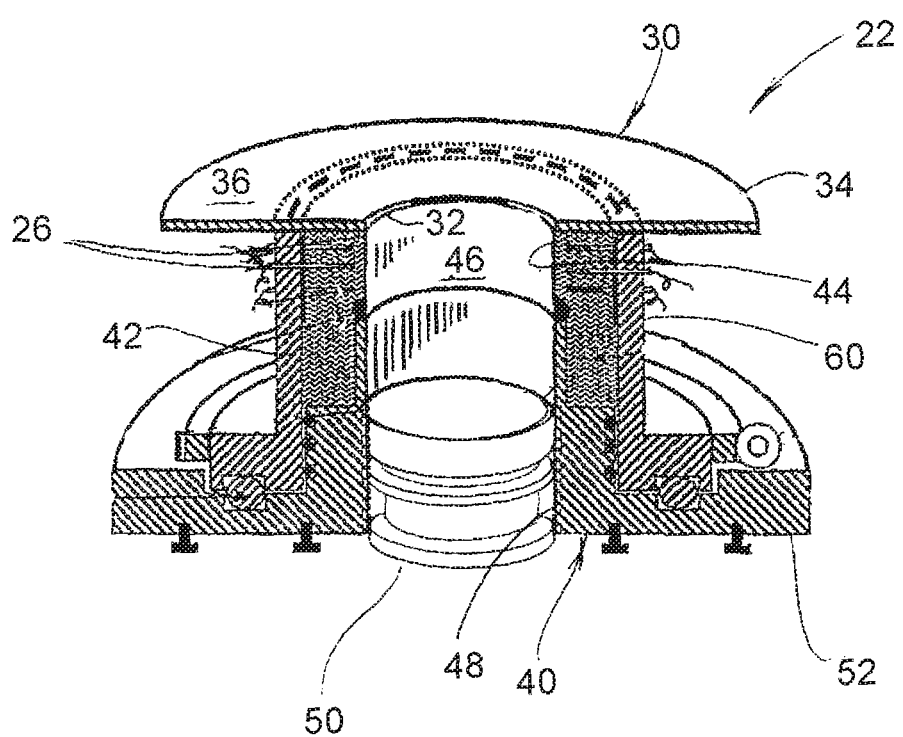
FIG. 2 is a perspective in partial section of an apparatus for constraining a breast according to one embodiment of the present invention.

As illustrated in FIG. 2, apparatus 22 of a first embodiment is designed to constrain soft tissue such as a human breast (not shown). The apparatus 22 includes an annular support, generally designated 30, support sized and shaped for contacting the patient around the breast. Although the support 30 may be made of other materials without departing from the scope of the present invention, in one embodiment the support is made from stainless steel. The support 30 of one embodiment has a circular central opening 32 and a circular outer edge 34. Although the support 30 may have other dimensions without departing from the scope of the present invention, in one embodiment the support has an inner diameter of between about 10 centimeters and about 20 centimeters, and an outer diameter of between about 20 centimeters and about 30 centimeters. As will be appreciated by those skilled in the art, the inner diameter may vary widely to accommodate different sized breasts. Further, it is envisioned that the shapes of the outer edge 34 and the central opening 32 may vary from circular in some embodiments. In one embodiment, the support 30 has a generally planar support surface 36 that contacts the patient around the breast in use. For convenience, this surface 36 will be referred to as an upper surface throughout this application, even though it should be understood that the apparatus 22 may be oriented so the surface faces sideways or downward without departing from the scope of the present invention. Likewise, other features will be described as upper (or lower) or referred to by a spatial orientation for convenience and that orientation is not the sole orientation the present invention may take.

As further illustrated in FIG. 2, the apparatus 22 includes a tubular, cylindrical body, generally designated by 40, mounted on the support 30 on a surface opposite the upper surface 36. The body 40 has a side wall 42 including an ultrasonically transparent upper portion 44 defining an interior 46 sized and shaped for receiving the breast of the patient when the support 30 contacts the patient around the breast. The side wall 42 of the body 40 also includes a lower portion 48 adjacent the upper portion 44. Although the body 40 may have other dimensions without departing from the scope of the present invention, in one embodiment the body has an inner diameter or width corresponding to the inner diameter of the support 30. Further, in the preferred embodiment the interior 46 of the body 40 and the opening 32 in the support 30 are aligned. Although the upper portion 44 and the lower portion 48 of the side wall 42 may be made of other materials without departing from the scope of the present invention, in one embodiment the upper portion is made of polyethylene or TPX that is as thin to provide minimal ultrasound attenuation through the wall and the lower portion is made of a strong material such as stainless steel. The inner diameters of the upper portion and the lower portion are the same and they are cemented together to form one cylinder with a smooth inside wall. A piston 50 is slideably mounted inside the lower portion 48 of the side wall 42. The piston 50 may be moved upward from the position shown in FIG. 2 toward the upper portion 44 of the cylindrical body 40 to position the breast in the interior of the upper portion as will be explained in greater detail below. The piston 50 may also be moved downward away from the upper portion 44 of the cylindrical body 40 to return it to the position shown in FIG. 2. As will be appreciated by those skilled in the art, the selectively moveable piston 40 renders a length and thus a volume of the interior 46 of the body selectively adjustable for matching a volume of the biological sample. In one embodiment, the lower portion 48 of the side wall 42 includes a flange 52 extending outward for mounting the body 40 to a base (not shown).

The apparatus 22 also includes a cylindrical mount 60 moveably mounted around the upper portion 44 of the body side wall 42 as further illustrated in FIG. 2. Each ultrasonic transducer 26 is mounted on the mount 60 so the transducers are positioned radially outward from the upper portion 44 body side wall 42 and can be moved simultaneously with respect to the body 40 (and enclosed tissue). One or more holes (not shown) are provided in the mount 60 for the installation of the ultrasonic transducers 26. Various means may be used for mounting the transducers 26 in the holes. In one embodiment, each hole is threaded to match an outer thread on the transducer. This embodiment has the advantage that a scanning radius of each transducer can be adjusted and locked. In one embodiment, the holes (and transducers) are distributed at different axial positions on the mount. Further, in one embodiment active portions of the transducers 26 are spaced from the inner surface of the mount 60 to avoid reflected acoustic waves.

Figure 3:
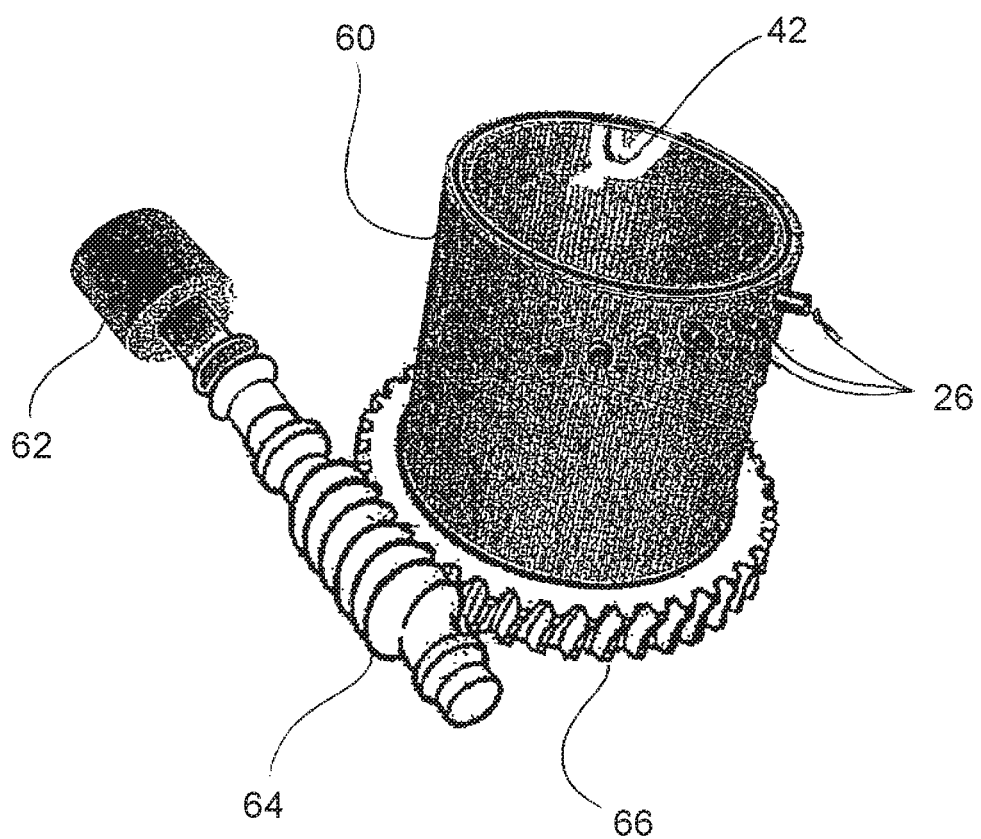
FIG. 3 is a perspective of a portion of the apparatus shown in FIG. 2 showing transducers in a first configuration.

Although it is envisioned that the mount 60 may move in other directions with respect to the body 40, in one embodiment, the mount rotates about an imaginary central axis A (FIG. 8) of the body so each transducer 26 orbits the interior 46 and any tissue contained therein. Various means may be used to rotate the mount 60 and transducers 26 with respect to the body 40. As shown in FIG. 3, one means for rotating the mount 60 with respect to the body 40 includes a motor 62 operatively connected to the mount. In one embodiment, the motor 62 is connected to a first gear, e.g., a worm screw 64, that engages a second gear, e.g., a worm gear 66. As will be appreciated by those skilled in the art, when the motor 62 turns the worm screw 64, the worm gear 66 turns the mount 60 and the transducers 26. The mount 60 may be driven by a step motor or servo motor through a variety of different transmissions including other gear trains and belts. In some embodiments, the mount 60 and the transducers 26 are rotatable through a full rotation (i.e., 2π). As these means for rotating the mount 60 are conventional, it will not be described in further detail.

Figure 4:
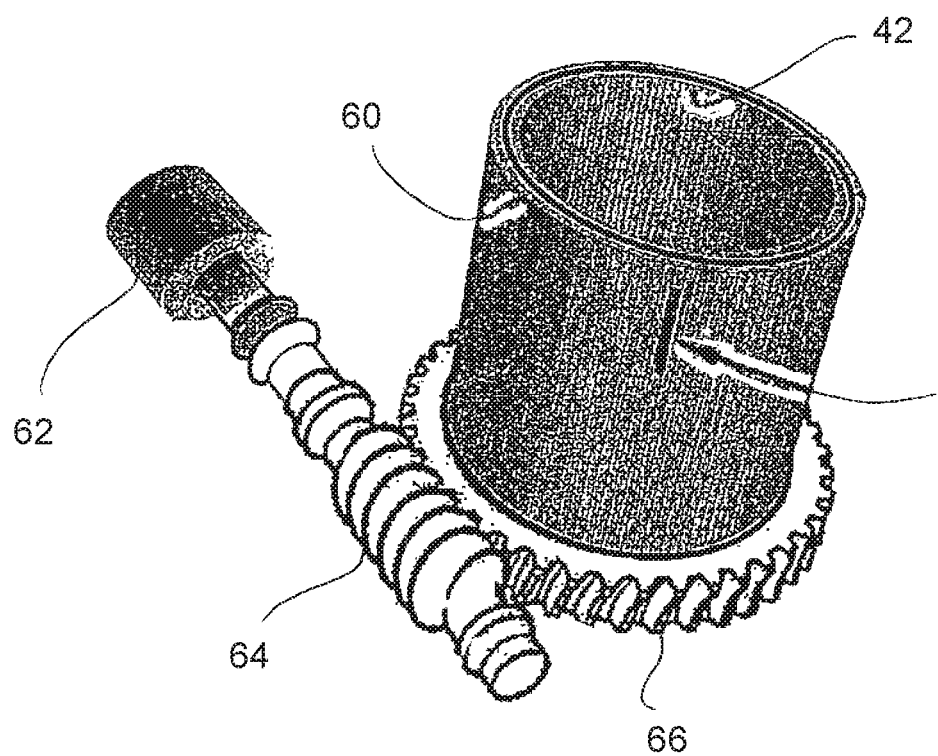
FIG. 4 is a perspective of a portion of the apparatus similar to FIG. 3 showing transducers in a second configuration.
Figure 5:
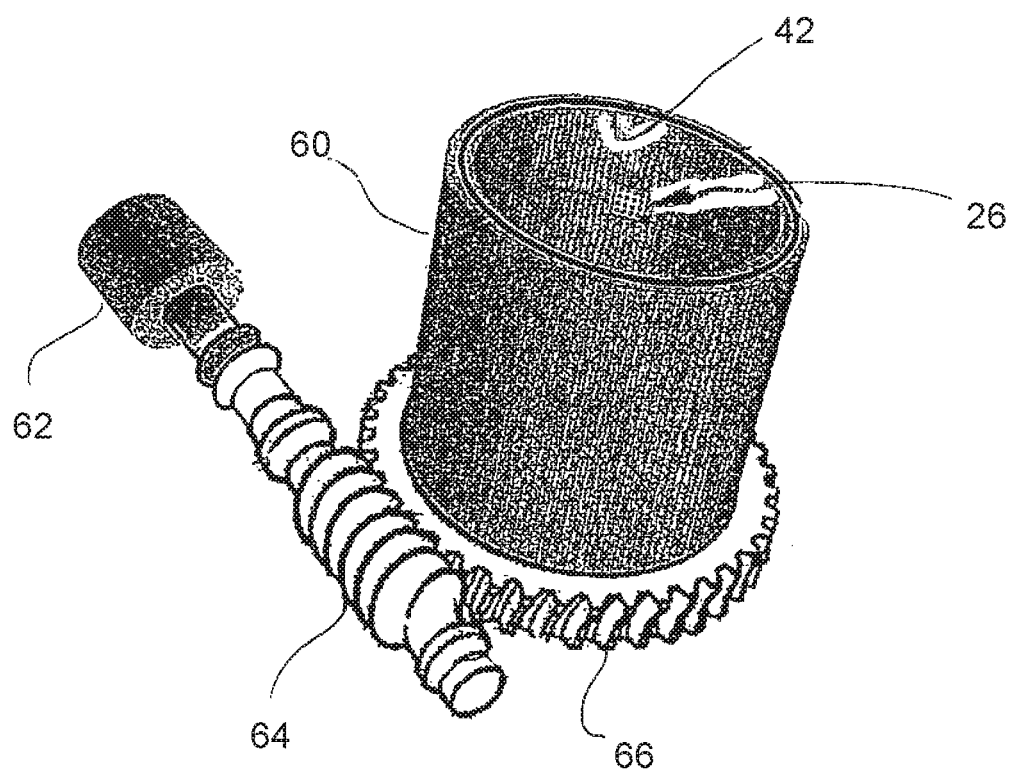
FIG. 5 is a perspective of a portion of the apparatus similar to FIG. 3 showing transducers in a third configuration.
Figure 6:
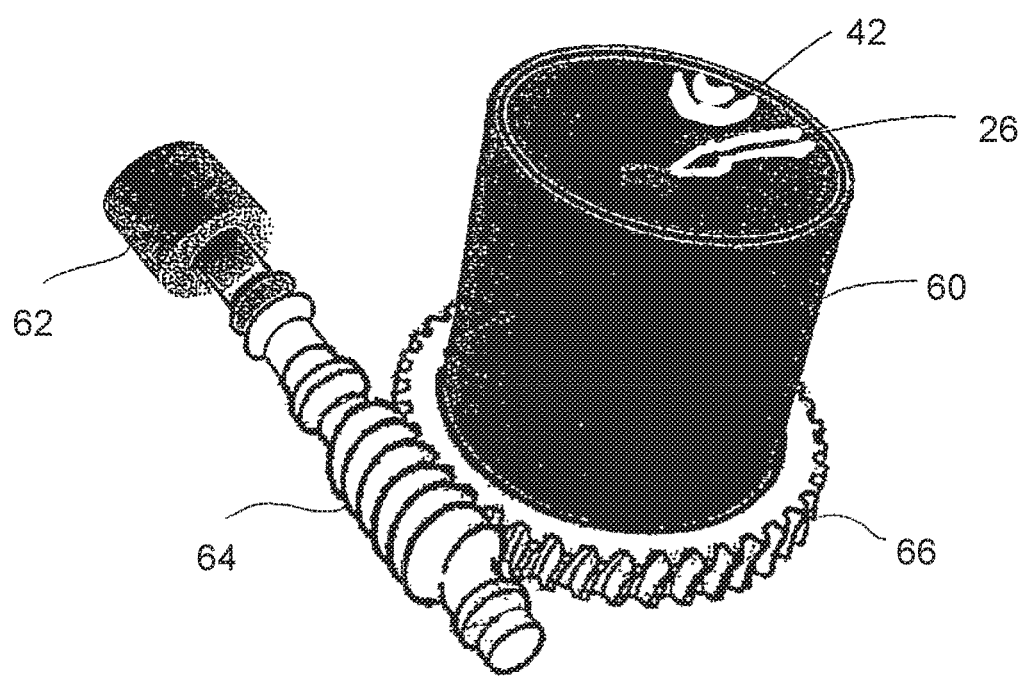
FIG. 6 is a perspective of a portion of the apparatus similar to FIG. 3 showing transducers in a fourth configuration.
Figure 7:
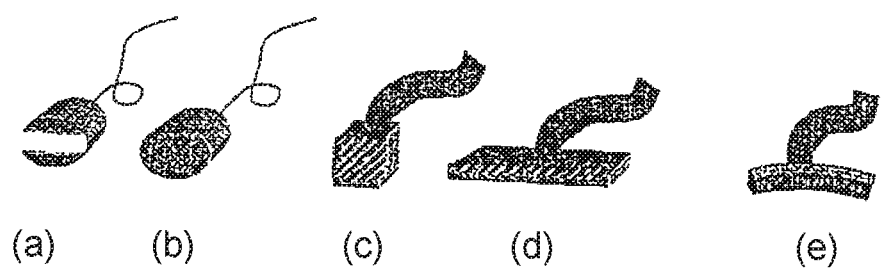
FIG. 7 shows ultrasonic transducers and arrays employed for imagining, according to embodiments of the present invention.

FIG. 3 also illustrates a first configuration in which the transducers 26 may be arranged. The transducers 26 in FIG. 3 are arranged in a helix. FIG. 4 illustrates a second configuration for the transducers 26 in which they are arranged in a straight line that is aligned with a central axis of the body 42. FIG. 5 illustrates a third configuration for the transducers 26 in which they are arranged in a planar two dimensional array. FIG. 6 illustrates a fourth configuration for the transducers 26 in which they are arranged in an arcuate two dimensional array. As will be appreciated by those skilled in the art, various conventional ultrasonic transducers (both singular transducers and transducer arrays) may be used for imaging without departing from the scope of the present invention. For example, FIG. 7 illustrates some of the various conventional types of ultrasound transducer set-ups that are envisioned: (a) the ultrasonic transducer cylindrically focused in the vertical dimension, (b) unfocused ultrasonic transducer, (c) two-dimensional or inner diameter linear or sector ultrasound array, (d) ultrasonic transducers at different frequency bands. Further, it is envisioned that the induced ultrasonic signals may be received by a stationary ring array of ultrasound transducers (not shown). As these configurations are conventional, they will not be described in further detail.

Figure 8:
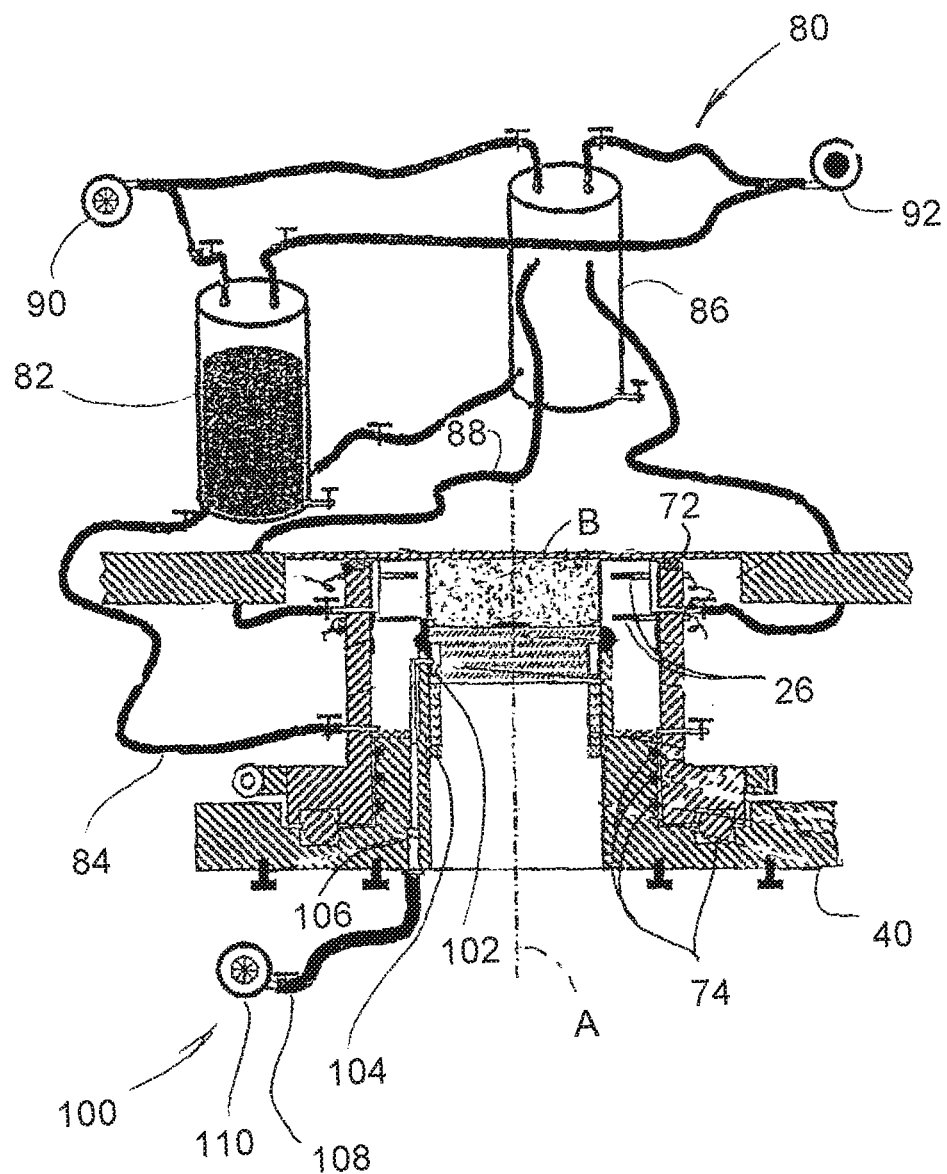
FIG. 8 is a cross section of an apparatus for constraining a breast according to second embodiment of the present invention, incorporating a subsystem for filling a chamber with coupling fluid.
Figure 9:
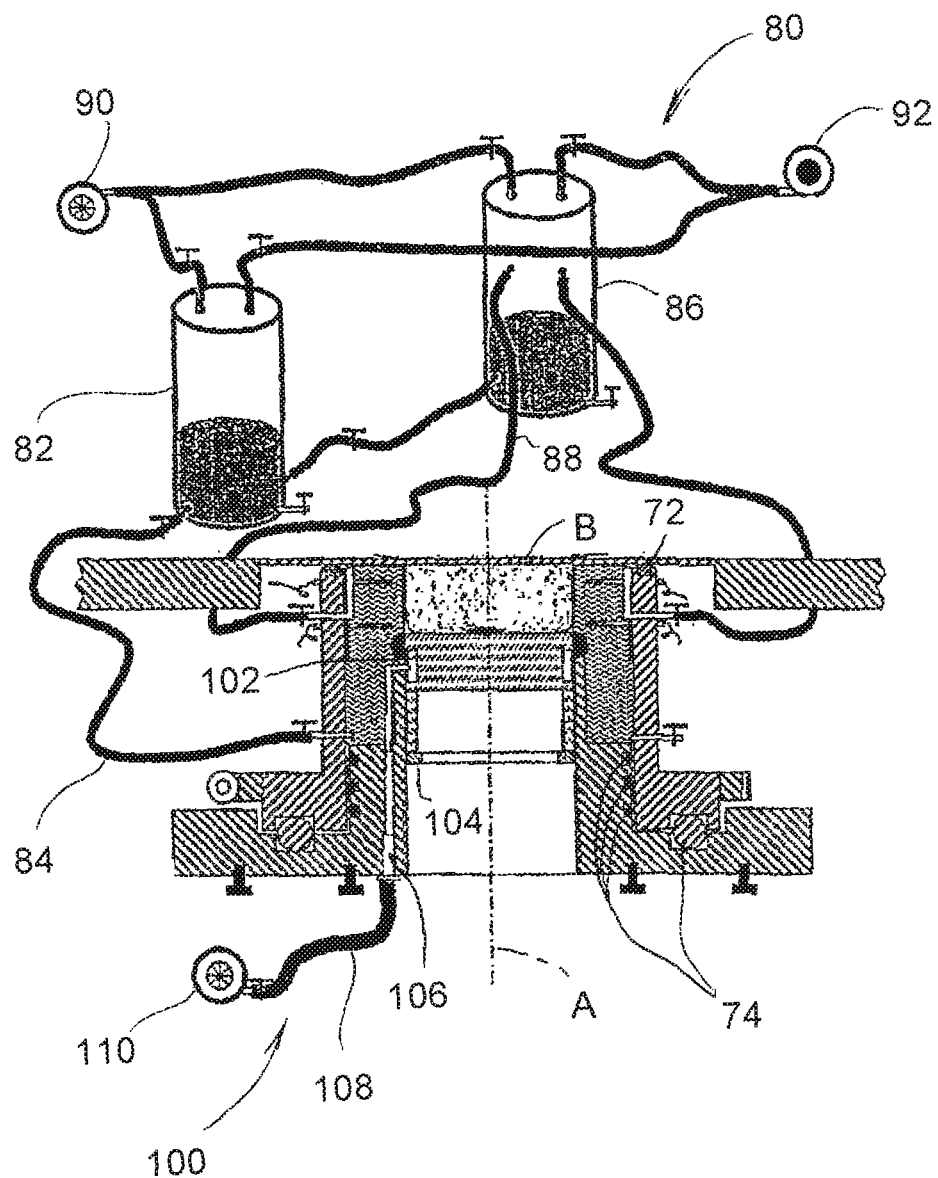
FIG. 9 is a cross section of the apparatus shown in FIG. 8 showing coupling fluid in the chamber.

As will be appreciated by those skilled in the art, several means may be used to improve measurements received from the transducer 26. One means includes acoustical absorbing material disposed on an inner surface of the mount 60 and the lower surface of the support 30 to reduce reflection of sound waves from these surfaces that cause scatter. Although other acoustical absorbing materials may be used without departing from the scope of the present invention, in one embodiment, the acoustical absorbing material is synthetic and natural rubbers. Another means for improving measurements received from the transducer 26 includes use of an acoustic coupling fluid between the mount 60 and the upper portion 44 of the side wall 42 of the body 40. Toward this end, a fluid tight chamber 70 may be provided between the mount 60 and the body 40 for retaining the coupling fluid as illustrated in FIGS. 8 and 9. A seal 72 is provided between the support 30 and the mount 60 at an upper end of the chamber 70 to prevent fluid from passing between them. Similarly, one or more seals 74 are provided between the body 40 and the mount 60 at a lower end of the chamber 70 to prevent fluid from passing between them.

As further illustrated in FIGS. 8 and 9, a subsystem, generally designated by 80, is provided in one embodiment for filling the chamber 70 with acoustic coupling fluid (or more broadly acoustic coupling media) and draining acoustic coupling fluid from the chamber. Although other acoustic coupling media may be used without departing from the scope of the present invention, in one embodiment the media may be deionized and distilled (DD) water. The subsystem 80 may also be advantageous to remove bubbles from the coupling fluid in the chamber 70 to prevent them from interfering with the transducer measurements. A first reservoir 82 is used to store the acoustic coupling medium and fill the coupling chamber 72 housing the ultrasonic transducers 26 through a line 84 entering the coupling chamber near its lower end. A second reservoir 86 is connected to the coupling chamber 72 through a line 88 entering the coupling chamber near its upper end and used to remove accumulated air bubbles and excess fluid in the coupling chamber. A vacuum pump 90 and a pressurizing pump 92 are connected to the reservoirs 82, 86 at their respective upper ends. A return line 94 with a valve 96 joins the two reservoirs 82, 86 at their respective lower ends.

A conventional ultrasound gel (not shown) may be applied to the breast B before it is positioned in the apparatus 22 to improve acoustic coupling. Further, as shown in FIGS. 8 and 9, a second subsystem, generally designated by 100, is provided to remove air from between the breast B and the side wall 42 of the apparatus 22 to still further improve quality acoustic coupling. An annular groove 102 is provided on the piston 50 adjacent its top and a fluid tight seal 104 is provided on the piston below the groove. The interface between the piston 50 and wall 42 is allows for fluid leakage. A passage 106 extending through the body 40 is connected by a line 108 to a vacuum pump 110. As will be appreciated by those skilled in the art, the vacuum pump 110 selectively draws air from the groove 102 to remove air from between the breast and body 40 so the breast conforms to the cylindrical shape of the body interior 46.

As mentioned above, equipment 24 is positioned axially downward from the piston 50 for directing radiation through the piston and into the breast to excite an ultrasonic response in the breast. It is this ultrasonic response that the transducers 26 measure. In some embodiments, the equipment 24 may comprise an electromagnetic source adapted to produce electromagnetic energy in a radiofrequency band, a microwave band, a visible light band, and/or an infrared light band.

Figure 10:
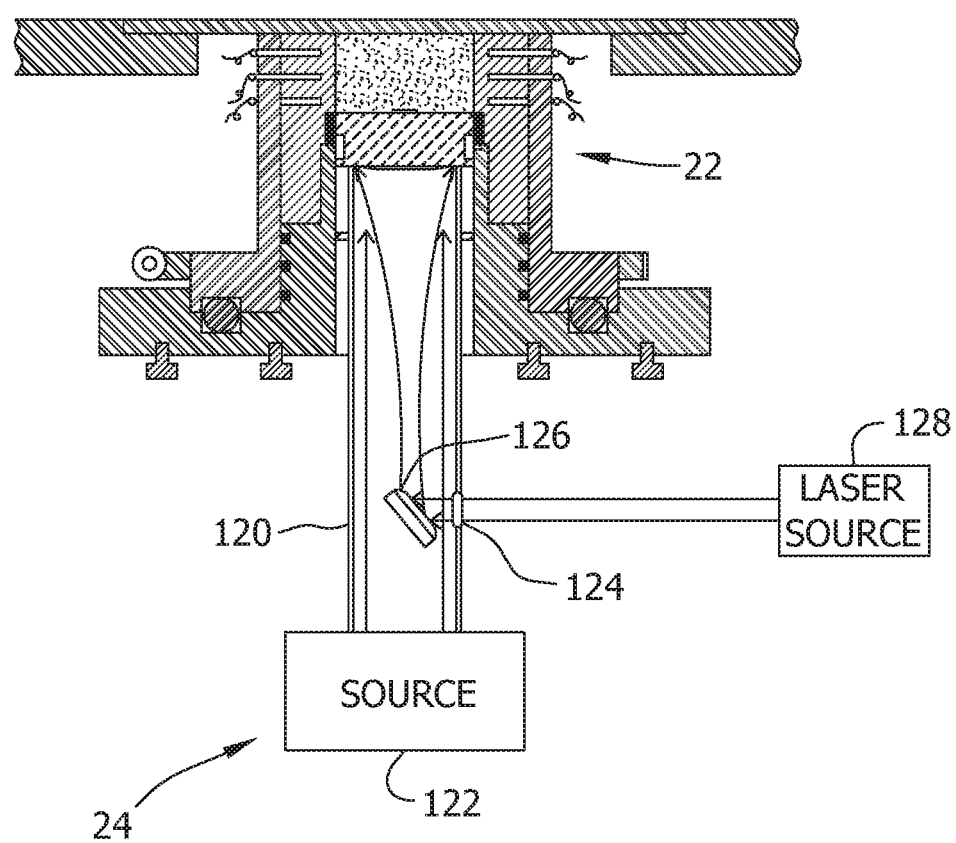
FIG. 10 is a cross section of an apparatus similar to that of FIG. 2 showing electromagnetic equipment of a first embodiment for delivering laser pulses and microwave pulses to a breast.

For example, as illustrated in FIG. 10, the electromagnetic equipment 24 delivers laser pulses and microwave pulses to a breast, which can be used to complete data acquisition for both photoacoustic and thermoacoustic tomography with one circular scan. The equipment 24 includes a waveguide 120 having a microwave source 122 at one end. Microwave energy emitted from the source 122 passes through the piston 50 and is delivered to the breast B directly. An optical window 124 is formed at a node along the waveguide 120. A dielectrically coated convex mirror 126 is positioned inside the waveguide 120 and aligned with the window 124. A laser source 128 is positioned outside the waveguide 120 and directs laser energy through the window 124 to the mirror 126 which expands the laser energy and directs it toward the breast B. Switching between microwave and laser excitation sources permits the acquisition of images with multiple contrasts from the different scans. As other features of this equipment 24 are conventional and understood by those skilled in the art, they will not be described in further detail.

Figure 11:
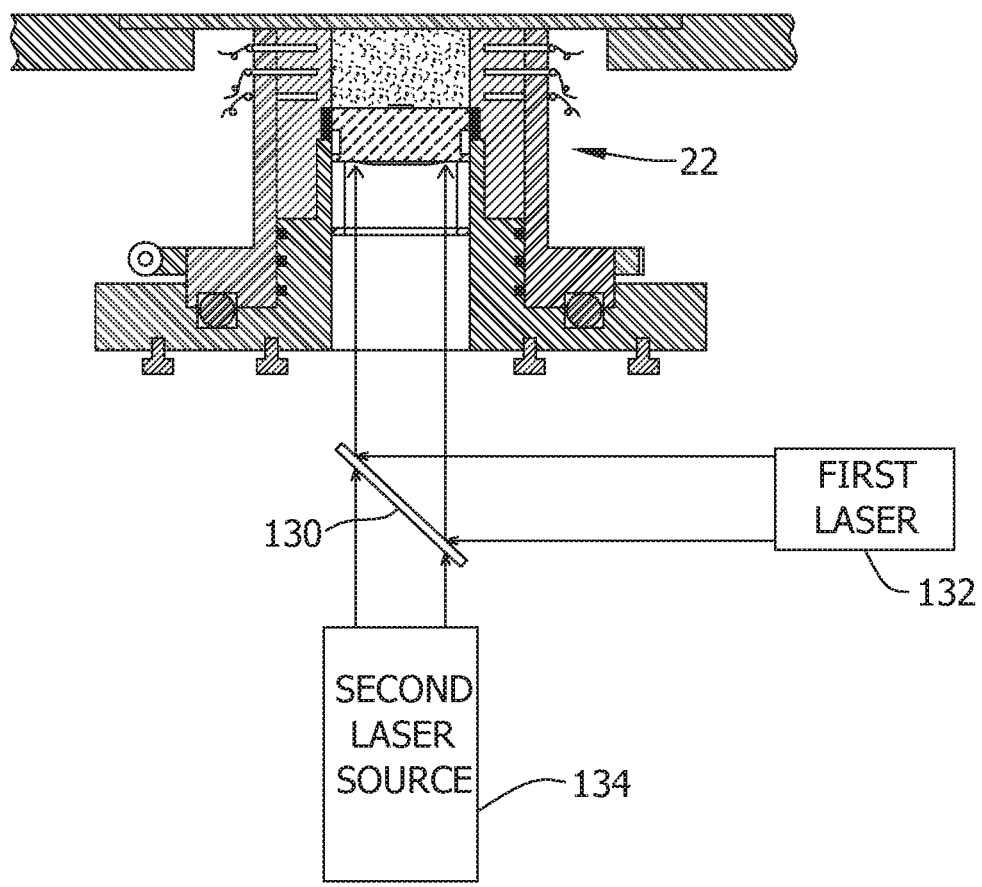
FIG. 11 is a cross section of an apparatus similar to that of FIG. 2 showing electromagnetic equipment of a second embodiment for delivering laser pulses of two wavelengths to a breast.

In the embodiment illustrated in FIG. 11, the electromagnetic equipment 24 delivers laser pulses of two wavelengths to a breast, which can be used to complete data acquisition for both photoacoustic and thermoacoustic tomography with one circular scan. A specially designed mirror 130 reflects laser energy from a first laser 132 to the breast while laser energy from a second laser 134 having a different wavelength from the first passes through the mirror to travel to the breast. This system allows for rapid switching between the two optical wavelengths.

Using the equipment described above with respect to FIGS. 10 and 11, complete photoacoustic and thermoacoustic tomography (FIG. 10) or multi-wavelength photoacoustic tomography (FIG. 11) can be accomplished with one circular scan so that images of multiple contrasts may be acquired simultaneously. Alternatively, two separate scans can be used in either configuration. As will be appreciated by those skilled in the art, at each scanning position a first trigger signal fires a pulse from one of the two excitation sources and triggers data acquisition of the induced acoustic wave. After the first induced acoustical signals die out, a second trigger signal starts another excitation pulse from second excitation source, for which data is then acquired.

Figure 12:
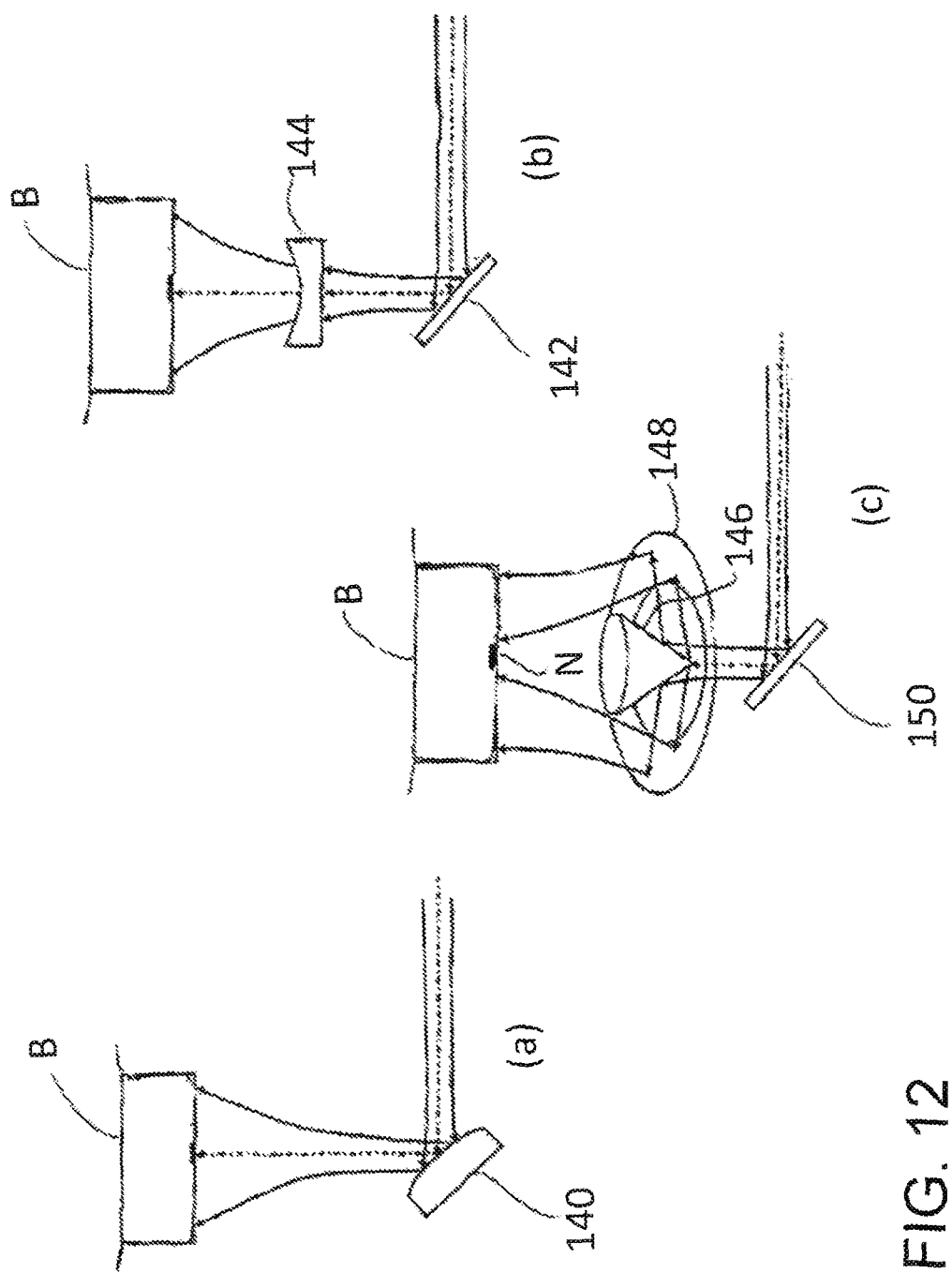
FIG. 12 shows various reflector and lens used for delivering electromagnetic energy to the tissue.

FIG. 12 illustrates various alternative configurations for delivering electromagnetic energy to the breast B. FIG. 12(a) illustrates the use of a convex reflector 140 to expand and direct laser light to a breast B. FIG. 12(b) illustrates the use of a mirror 142 and a concave lens 144 to expand and direct laser light to a breast. FIG. 12(c) illustrates the use of a combination of a cone reflector 146 and a frustoconical ring reflector 148 and a mirror 150 to form a ring laser beam. For microwave pulses, a waveguide or an antenna may be used. For laser pulses, a beam expander, such as a convex reflector or a mirror and a concave lens, may be used as illustrated in FIGS. 12(a)&(b). To avoid illuminating a nipple N and to minimize light energy loss, a combination of cone and ring reflectors may be employed to form a ring beam as shown in FIG. 12(c).

Various electromagnetic sources may be used. In one embodiment, short pulses of electromagnetic radiation, such as microwave pulses or laser pulses, may be employed to induce thermoacoustic or photoacoustic signals in human breast tissue. The following examples are illustrative (and not exhaustive) of sources which may be used as excitation for imaging purposes:
1. A 3-GHz microwave generator with a pulse energy of approximately 10 mJ and a pulse width of 0.1 µs, 0.5 µs, and 1.0 µs, respectively.
2. A 9-GHz microwave generator with a pulse energy of approximately 10 mJ and a pulse width of 0.1 µs, 0.5 µs, and 1.0 µs, respectively.
3. A Q-switched Nd:YAG laser working at the fundamental or second harmonic wavelength of 1064 nm or 532 nm, respectively, pulse width of approximately 7 ns or 10 ns, respectively. Energy densities on test samples are controlled within the ANSI safety limits.
4. A dye laser pumped by a Q-switched Nd:YAG laser. The laser line is tunable from 540 nm to 900 nm and has a pulse width of approximately 7 ns.
5. A Ti:Sapphire laser pumped by a Q-switched Nd:YAG laser. The laser line is tunable from 690 nm to 1000 nm and has a pulse width of approximately 10 ns.

Although the apparatus 22 may be mounted in other positions without departing from the scope of the present invention, in one embodiment the apparatus is mounted adjacent an opening in a surface that is sized, shaped and positioned for receiving the soft tissue. For example, an examining table (not shown) may include an upper surface having openings therein for receiving the patient's breasts. In this embodiment, the patient would lie face down on the table so her breast is positioned in the opening. In alternative embodiments, the surface may be a vertical surface or a horizontal surface oriented so the patient rests on her back and the surface compresses the breasts from above. As will be appreciated from the description provided above, an imaging system mounted beneath the examining table bed. Ultrasound gel is applied to the surface of the breast to achieve better acoustic coupling with the apparatus. Alternatively, water can be applied to the inner wall of the apparatus to improve acoustic coupling. Apparatus 22 beneath the opening holds the breast as shown in FIG. 13(a) so the upper portion of the apparatus body is in contact with the breast and the support contacts the patient around the breast.

Figure 13:
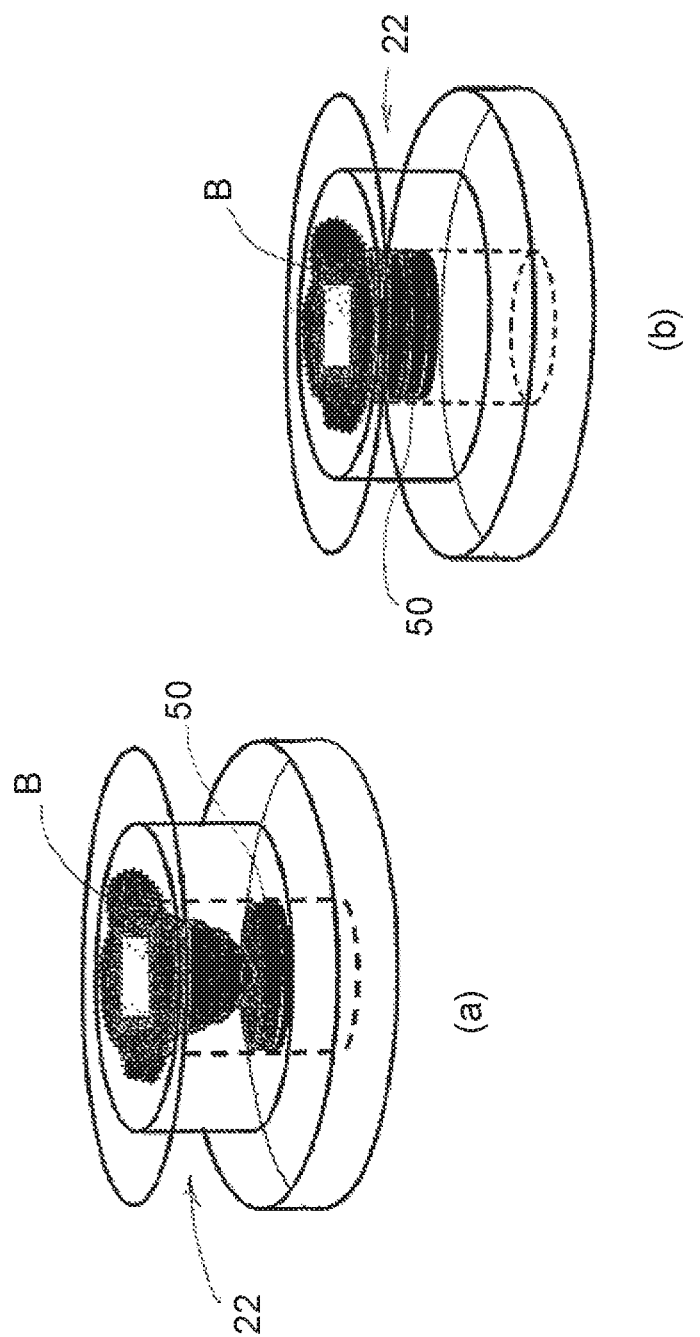
FIG. 13 is a schematic perspective of apparatus of the present invention as the breast is loaded.

After the breast is suspended in the cylinder, the piston 50 is moved upward so it gently pushes the breast upward against the chest wall as shown in FIG. 13(b). The breast is then confined and formed to a cylindrical shape by the ultrasonically transparent upper portion of the apparatus wall. The fluid subsystem 100 may be energized to remove air from between the breast and the apparatus wall to achieve the cylindrical shape. The cylindrical shape reduces the thickness of the breast in the propagation direction of the radiation in order to minimize attenuation of electromagnetic energy, maintain a relatively uniform electromagnetic excitation of photoacoustic/thermoacoustic waves on each imaging plane, to improve acoustic coupling, and to reduce motion artifacts. Unlike the lateral compression required by x-ray mammography, compression against the chest wall poses little discomfort. The laser or microwave excitation radiation illuminates the breast from the bottom through the transparent piston with little energy loss.

The following steps are taken to fill the coupling chamber and remove air bubbles from the coupling chamber. Driven by the vacuum pump, the fluid-filling reservoir is used to remove the fluid in the coupling chamber to a level below the inlet at its bottom. With the fluid inlet to the coupling chamber shut off, the vacuum pump is used to remove air from the acoustic coupling medium in the fluid-filling reservoir, from the fluid-draining reservoir, and from the coupling chamber as well. With the vacuum inlet to the fluid-filling reservoir closed, high pressure from the pressure pump is applied to the filling reservoir while low pressure from the vacuum pump is still applied to the draining reservoir; the fluid inlet to the coupling chamber is turned on to fill the vacuumed coupling chamber with bubble-free fluid. The fluid can be further circulated to the fluid-draining reservoir, where any spare bubbles can be removed. When the fluid in the filling reservoir decreases to a preset level, the filling valve is shut off, the filling reservoir is vacuumed, pressure is applied to the draining reservoir and the valve connecting the two reservoirs is opened to transfer fluid from the draining reservoir to the filling reservoir. The above procedures are repeated until the bubbles trapped in the circulation loop are completely removed. The coupling chamber is filled with bubble-free fluid and the fluid inlet to the coupling chamber is shut off. A heater (not shown) may be provided to warm the fluid to human body temperature or a similar comfortable temperature.

Once the chamber is filled and the breast is in position, the following occurs: (a) the motor begins to move the ultrasound transducers to their initial pre-arranged positions; (b) a trigger signal is generated to fire electromagnetic pulses (laser or microwave) and trigger the data acquisition of the induced acoustic signals; and (c) the ultrasound transducers move to the next scanning stop. Steps b and c are repeated until the scanning is completed completely around the circumference of the breast.

Figure 14:
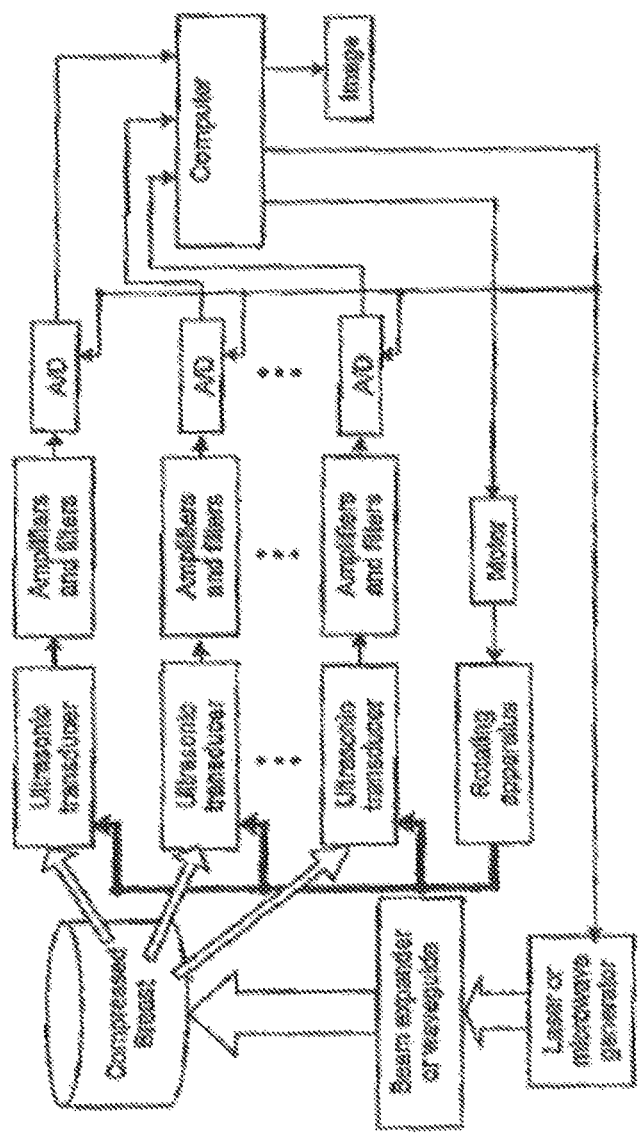
FIG. 14 is a schematic diagram showing a signal excitation and data acquisition sequence, according to one embodiment of the present invention.

FIG. 14 illustrates a signal excitation and data acquisition sequence, according to one embodiment of the present invention. For continuous scanning, the follow occurs: (a) a sync signal generated by a computer starts the continuous circular scanning of the ultrasound transducers, driven by a motor; (b) upon starting, a series of trigger signals, with a fixed pulse rate, are generated to simultaneously trigger the electromagnetic pulses emission (laser or microwave) and the data acquisition of the induced acoustic signals; and (c) when the circular scanning around the entire perimeter of the breast completed, both the motor and the trigger-signal generation stop. In multi-channel parallel data acquisition, for each channel, an ultrasonic transducer is selected based on the desired sensitivity and resolution. Then, corresponding preamplifiers, filters and amplifiers are chosen for each channel. The induced acoustic signals are digitized by analog-to-digital boards (A/D) and recorded in the memory.

Induced acoustic signals may be enhanced using contrast agents, such as indocyanine-green for photoacoustic imaging.

The following are non-exhaustive example uses of various embodiments of the present invention. Using 3-GHz microwave pulses, malignant tumors (such as infiltrating lobular carcinomas or invasive metaplastic carcinomas with chondroid and squamous metaplasia) may be detected. For each case, the position, shape and size of the carcinoma may be revealed and verified by corresponding digital radiographs and sonograms of the same specimen. Using laser pulses, tumor-associated angiogenesis in rat brains may be observed. The photoacoustic images of rat brain tumors reveal the angiogenesis that is associated with tumors. Further, brain tumors can be identified based on their distorted vascular architecture, related vasculature changes; and evidence of hemorrhage. Although optical penetration is maximized with near-infrared laser pulses of 800 nm in wavelength, the optical contrast may be enhanced by indocyanine green (ICG) having an absorption peak matching the laser wavelength. This optimized photoacoustic tomography has been found to image objects embedded at a depth of up to 5.2 cm, 6.2 times the 1/e effective optical penetration depth, in chicken breast muscle at a resolution of better than 780 microns and a sensitivity of better than 7 pmol of ICG in blood.

Certain embodiments may provide a number of technical advantages. For example, a technical advantage of one embodiment may include the capability to slightly compress the breast against the chest wall to form a nearly cylindrical shape that reduces the thickness of the breast in the direction of the electromagnetic wave propagation, improves acoustic coupling, and reduces motion artifacts. With such a configuration, each image slice may have a more uniform distribution of excitation energy because of the approximate cylindrical shape of the compressed breast.

Other technical advantages of other embodiments may include the capability to simultaneously scan multiple (either different or identical) ultrasonic transducers at different vertical positions around the breast in circular orbits and employ parallel multi-channel detections. The electronics for each detection channel may be built according to the corresponding transducer's characteristics. Using ultrasonic transducers that are cylindrically focused in the vertical direction may increase imaging resolution in the vertical direction. In the prone orientation described above, the transducers distributed at various heights around the breast from its bottom to its top near the chest wall provide multiple two-dimensional cross-sectional images at various heights. Accordingly, the design may allow for diversity in the use of ultrasonic transducers. For example, at one height multiple transducers of different bandwidths may be used to simultaneously image the tissue structures in that particular layer. In this way, both imaging sensitivity and resolution are ensured because there is a tradeoff between the two when the bandwidth is varied.

Yet further technical advantages of some embodiments may include the capability to scan an ultrasonic array, such as a linear array, a sector array, or a two dimensional array, in a circular orbit to improve the image quality. In such an embodiment, a contrived circular scanning of an array may be made of many small active elements. Such a contrivance may ensure good spatial resolution in a large imaged breast volume and sufficient acoustical sensitivity.

Yet another technical advantage of some embodiments may include the capability to expand and deliver laser and microwave energy to the breast with designs having minimal energy loss.

Still another technical advantage of other embodiments may include the capability to implement precise circular scanning of detectors.

Yet other technical advantages of some embodiments may include the capability to remove air bubbles from ultrasound propagating medium.

Other technical advantages of some embodiments may include the capability to scan detectors continuously while induced acoustic signals from multiple channels are acquired in parallel. The detectors may also be scanned step-by-step with data acquired at each scan stop.

Yet further technical advantages of other embodiments may include the capability to acquire complete data for photoacoustic and thermoacoustic tomography or multi-wavelength photoacoustic tomography within one circular scan resulting in multiple images of optical and microwave contrasts. Optical contrast at multiple laser wavelengths can also be acquired simultaneously. The design may also switch between photoacoustic tomography and thermoacoustic tomography by changing the excitation source to either laser or microwave.

Another technical advantage of some embodiments may include the capability to add ultrasound absorbers to the inner wall surrounding the acoustic coupling medium to minimize ultrasound reflection.

According to teachings of some embodiments of the invention, a human breast is imaged with high spatial resolution and high contrast. The contrast may be based primarily on the difference in the absorption coefficients of different biological tissues when exposed to optical or electromagnetic radiation (although mechanical properties may also sometimes contribute to image contrast). Although an improved accuracy in the detection of breast cancer is a benefit that may avail from teachings of some embodiments of invention, other benefits may avail from teachings of other embodiments of the invention. Accordingly, although breast tissue will be described with reference to some embodiments, it should be understood that other embodiments may be used for other purposes.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A system to perform photoacoustic/thermoacoustic imaging of a human breast, the system comprising:
   a cylindrical body comprising a side wall, the side wall comprising a cylindrical inner wall defining an interior, the side wall further comprising:
   an ultrasonically transparent upper portion comprising an upper opening configured to receive and confine the human breast within the interior; and
   a lower portion opposite the ultrasonically transparent upper portion, the lower portion configured to receive a piston;

wherein the cylindrical body is configured to confine the human breast within the interior;

a cylindrical mount moveably mounted around and radially outward from the ultrasonically transparent upper portion of the side wall, wherein the cylindrical mount is inhibited from rotation with respect to the cylindrical body;

a ring array of ultrasound transducers mounted on the cylindrical mount, the ring array of ultrasound transducers configured to receive induced ultrasonic signals from within the interior via the ultrasonically transparent upper portion;

the piston slideably mounted within the lower portion of the cylindrical body side wall, the piston configured to move upward to compress the human breast against a chest wall positioned over the upper opening and to confine the human breast into a cylindrical shape conforming to the inner wall when the human breast is received into the interior; and an electromagnetic source configured to produce a plurality of electromagnetic energy pulses and to direct the electromagnetic energy pulses directed into the interior.

2. The system of claim 1, wherein at least a portion of the piston is transparent to the plurality of electromagnetic energy pulses.

3. The system of claim 2, wherein the electromagnetic source is positioned axially downward from the piston.

4. The system of claim 3, wherein:
the electromagnetic source comprises a microwave source coupled to a waveguide;
the microwave source is configured to produce a plurality of microwave energy pulses; and
the waveguide is configured to direct a plurality of microwave pulses through the piston into the interior.

5. The system of claim 4, wherein:
the waveguide further comprises a window positioned at a node along the waveguide and a convex mirror positioned within the waveguide;
the electromagnetic source further comprises a laser source configured to produce a plurality of laser pulses directed to the convex mirror; and the convex mirror is configured to reflect the plurality of laser pulses into the interior via the waveguide and is further configured to expand the plurality of laser pulses.

6. The system of claim 5, wherein the electromagnetic source is further configured to produce a microwave energy pulse and a laser energy pulse in an alternating and repeating sequence.

7. The system of claim 2, wherein the electromagnetic source comprises a laser source configured to produce a plurality of laser pulses and a mirror configured to direct the plurality of laser pulses into the interior.

8. The system of claim 7, wherein the mirror is a convex reflector configured to expand the plurality of laser pulses.

9. The system of claim 7, wherein the mirror comprises a cone reflector and a frustoconical ring reflector configured to form a ring laser beam directed into the interior.

10. The system of claim 7, wherein:
the electromagnetic source comprises a second laser source configured to produce a second plurality of laser pulses directed into the interior;
the mirror is further configured to transmit the second plurality of laser pulses; and
the second plurality of laser pulses comprise a second wavelength different from a wavelength of the plurality of laser pulses.

11. The system of claim 10, wherein the electromagnetic source is further configured to produce a laser energy pulse and a second laser energy pulse in an alternating and repeating sequence.

12. The system of claim 1, further comprising:
a vacuum pump operatively coupled to a vacuum line at a first end; and
the vacuum line further comprising a second end opposite to the first end, the second end operatively coupled to a passage formed through the cylindrical body into the interior;
wherein the vacuum pump is configured to remove air from the interior after the human breast is received into the interior.

13. The system of claim 1, wherein the upper portion of the side wall comprises an ultrasonically transparent material selected from:
polyethylene, TPX, and any combination thereof.

14. The system of claim 1, wherein the system further comprises an amount of an acoustical absorbing material disposed radially outward of at least a portion of the side wall opposite the interior.

15. The system of claim 14, wherein the acoustical absorbing material is selected from a synthetic rubber, a natural rubber, and any combination thereof.

* * * * *